US009126983B2

(12) United States Patent
Singh et al.

(10) Patent No.: US 9,126,983 B2
(45) Date of Patent: Sep. 8, 2015

(54) EXTRACTS FROM KIBDELOS PORANGIUM AS ANTIBACTERIAL AGENTS

(75) Inventors: Sheo Singh, Edison, NJ (US); Jon D. Polishook, Old Bridge, NJ (US); Deborah L. Zink, Manalapan, NJ (US); Olga Genilloud, Madrid (ES); Michael Goetz, Scotch Plains, NJ (US); Francisca Vicente, Madrid (ES); David Brian Olsen, Lansdale, PA (US); Scott Knoble Smith, San Jose, CA (US)

(73) Assignees: Merck Sharp & Dohme Corp., Rahway, NJ (US); Merck Sharp & Dohme de Espana SA, Madrid (ES)

( * ) Notice: Subject to any disclaimer, the term of this patent is extended or adjusted under 35 U.S.C. 154(b) by 233 days.

(21) Appl. No.: 13/518,613

(22) PCT Filed: Dec. 17, 2010

(86) PCT No.: PCT/US2010/060923
§ 371 (c)(1),
(2), (4) Date: Jun. 22, 2012

(87) PCT Pub. No.: WO2011/079034
PCT Pub. Date: Jun. 30, 2011

(65) Prior Publication Data
US 2013/0005673 A1    Jan. 3, 2013

Related U.S. Application Data

(60) Provisional application No. 61/306,572, filed on Feb. 22, 2010.

(30) Foreign Application Priority Data

Dec. 23, 2009   (ES) .................................. 200931252

(51) Int. Cl.
| C07H 15/26 | (2006.01) |
| A61P 31/04 | (2006.01) |
| A61K 31/706 | (2006.01) |
| A61K 31/7056 | (2006.01) |
| A01N 43/86 | (2006.01) |
| A01N 43/36 | (2006.01) |
| C07D 407/14 | (2006.01) |
| A61K 31/535 | (2006.01) |
| A61K 31/4025 | (2006.01) |
| C07D 413/14 | (2006.01) |
| C12P 17/16 | (2006.01) |
| C12R 1/01 | (2006.01) |

(52) U.S. Cl.
CPC .............. *C07D 407/14* (2013.01); *A01N 43/36* (2013.01); *A01N 43/86* (2013.01); *A61K 31/4025* (2013.01); *A61K 31/535* (2013.01); *C07D 413/14* (2013.01); *C12P 17/16* (2013.01); *C12R 1/01* (2013.01)

(58) Field of Classification Search
None
See application file for complete search history.

(56) References Cited

U.S. PATENT DOCUMENTS

| 4,548,974 A | 10/1985 | Bowie et al. |
| 8,742,135 B1 | 6/2014 | Igarashi et al. |

FOREIGN PATENT DOCUMENTS

| EP | 0132118 A2 | 1/1985 |
| EP | 0132118 B1 | 10/1989 |
| EP | 2471788 A1 | 7/2012 |
| EP | 2471788 B1 | 11/2013 |
| JP | 2009 203195 A | 9/2009 |
| JP | 2011-46622 | 3/2011 |

OTHER PUBLICATIONS

"Prevent", WordNet Search 3.0, also available at http://wordnet.princeton.edu; last accessed Aug. 2014.*
Scaglione, Francesco, The Pediatric Infectious Disease Journal, "Predicting the clinical efficacy of antibiotics: toward definitive criteria", Mar. 1997, vol. 16, No. 3, pp. S56-S59.*
Honma, T. et al., machine translation of JP 2009-203195, translation accessed Sep. 17, 2014.*
Ratnayake Ranjala et al, "Isokibdelones: Novel heterocyclic polyketides from a *Kibdelosporangium* sp.", Organic Letters, vol. 8, No. 23, pp. 5267-5270 (2006).
International Search Report in PCT/US2010/060923, mailed Feb. 17, 2011.
F. D. Lowy, Antimicrobial resistance: the example of *Staphylococcus aureus*, 111(9) J. Clinical Investigation 1265 (2003).
George Talbot et al., Bad Bugs Need Drugs: An Update on the Development Pipeline from the Antimicrobial Availability Task Force of the Infectious Disease Society of America, 42 Clinical Infectious Diseases 657 (2006).
Brad Spellberg et al, The Epidemic of Antibiotic-Resistant Infections: A Call to Action for the Medicinal Community from the Infectious Disease Society of America, 46 Clinical Infectious Diseases 155 (2007).
Methods for Antimicrobial Susceptibility Testing of Anaerobic Bacteria; Approved Standard—Seventh Edition. CLSI document M11-A7 [ISBN 1-56238-626-3], Clinical and Laboratory Standards Institute, 940 West Valley Road, Suite 1400, Wayne, Pennsylvania 19087-1898 USA (2007).

* cited by examiner

*Primary Examiner* — Layla Bland
*Assistant Examiner* — Bahar Craigo
(74) *Attorney, Agent, or Firm* — Laura M. Ginkel; Julie M. Lake

(57) ABSTRACT

The present invention relates to novel compounds of formulae (I) and (II) and pharmaceutically acceptable salts thereof that are useful in the treatment and/or prevention of human and animal bacterial infections and associated diseases and conditions; compositions containing such compounds; derivation of such compounds by fermentation and isolation, partial synthesis and total synthesis; methods of inhibiting bacterial growth; methods of treating, preventing or controlling bacterial infection; biologically pure cultures of bacterial strains from which such compounds may be produced; and processes for preparing compositions containing such compounds.
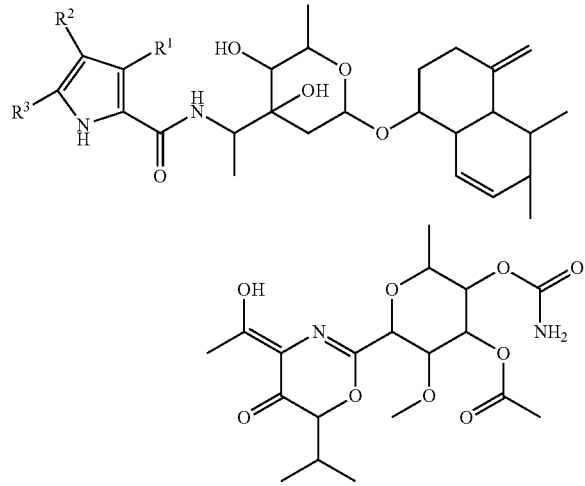
(I)
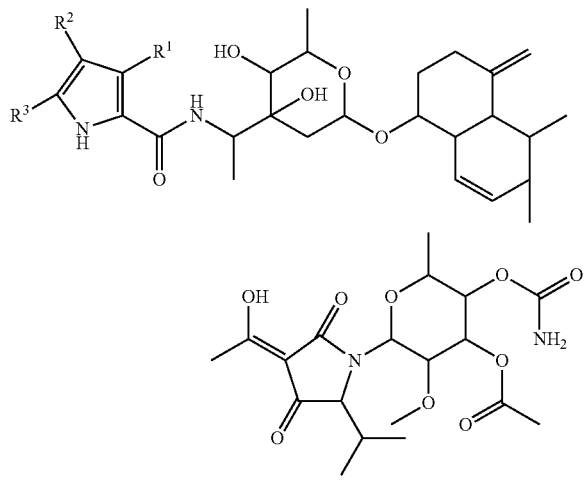
(II)
5 Claims, 3 Drawing Sheets

EXTRACTS FROM KIBDELOS PORANGIUM AS ANTIBACTERIAL AGENTS

CROSS-REFERENCE TO RELATED APPLICATIONS

This application is a National Stage application of International Patent Application No. PCT/US2010/060923, filed Dec. 17, 2010, which claims priority to U.S. Provisional Patent Application No. 61/306,572, filed Feb. 22, 2010, and to Spanish Patent Application No. P200931252, filed Dec. 23, 2009.

FIELD OF THE INVENTION

The present invention relates to novel compounds and pharmaceutically acceptable salts thereof; compositions containing such compounds; derivation of such compounds by fermentation and isolation, partial synthesis and total synthesis; methods of inhibiting growth of bacteria; methods of treating, preventing or controlling bacterial infection; biologically pure cultures of bacterial strains from which such compounds may be produced; and processes for preparing compositions containing such compounds. The novel compounds of this disclosure, their pharmaceutically acceptable salts, and compositions comprising such compounds and pharmaceutically acceptable salts, are useful for treating and/or preventing bacterial infections and associated diseases and conditions.

BACKGROUND OF THE INVENTION

Infections caused by bacteria are a growing medical concern as many of bacterial pathogens have become resistant to various common antibiotics. Such microbes include *Staphylococcus aureus, Staphylococcus epidermidis, Staphylococcus hemolyticus, Streptococcus pyogenes, Streptococcus pneumoniae, Enterococcus faecalis, Enterococcus faecium, Haemophilus influenzae, Pseudomonas aeruginosa, Acinetobacter calcoaceticus, Escherichia coli, Stenotrophomonas maltophilia, Clostridium difficile* and other pathogenic bacteria. See F. D. Lowy, *Antimicrobial resistance: the example of Staphylococcus aureus*, 111(9) J. CLINICAL INVESTIGATION 1265 (2003); George Talbot et al., *Bad Bugs Need Drugs: An Update on the Development Pipeline from the Antimicrobial Availability Task Force of the Infectious Disease Society of America*, 42 CLINICAL INFECTIOUS DISEASES 657 (2006); Brad Spellberg et al., *The Epidemic of Antibiotic-Resistant Infections: A Call to Action for the Medical Community from the Infectious Disease Society of America*, 46 CLINICAL INFECTIOUS DISEASES 155 (2007). In spite of the need for new antibacterial compounds, effective against such multi-drug resistant organisms and the intense efforts applied to this field, very few new antibiotic compounds have been approved by the FDA.

Thus, there remains a need for potent antibiotic agents that inhibit the growth of bacteria including bacteria that are resistant to known antibiotics.

SUMMARY OF THE INVENTION

The present invention relates to compounds that are selected from the group consisting of compounds of formula I and formula II:

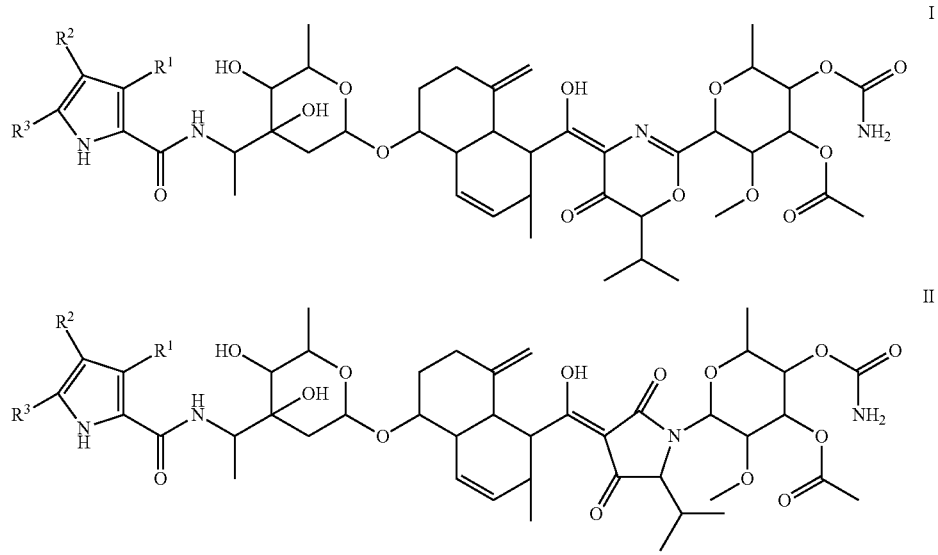

and pharmaceutically acceptable salts thereof, wherein:

$R^1$ and $R^2$ are independently selected from the group consisting of hydrogen and halogen; and $R^3$ is selected from the group consisting of hydrogen and $C_1$-$C_6$ alkyl groups.

These compounds are potent antibiotic agents with broad spectra of activity and can be used against pathogens associated with human and animal bacterial infections.

Additional aspects of the invention relate to compositions comprising mixtures of the compounds of the invention and pharmaceutical compositions and formulations that comprise a compound of the invention. In addition, aspects of the invention relate to methods of preparing a compound of the invention, to methods of inhibiting growth of bacteria, to methods of treating or preventing bacterial infection in humans and animals using a compound of the invention, and to methods of controlling bacterial infection in humans and animals using a compound of the invention.

DETAILED DESCRIPTION OF THE INVENTION

Figure 1:
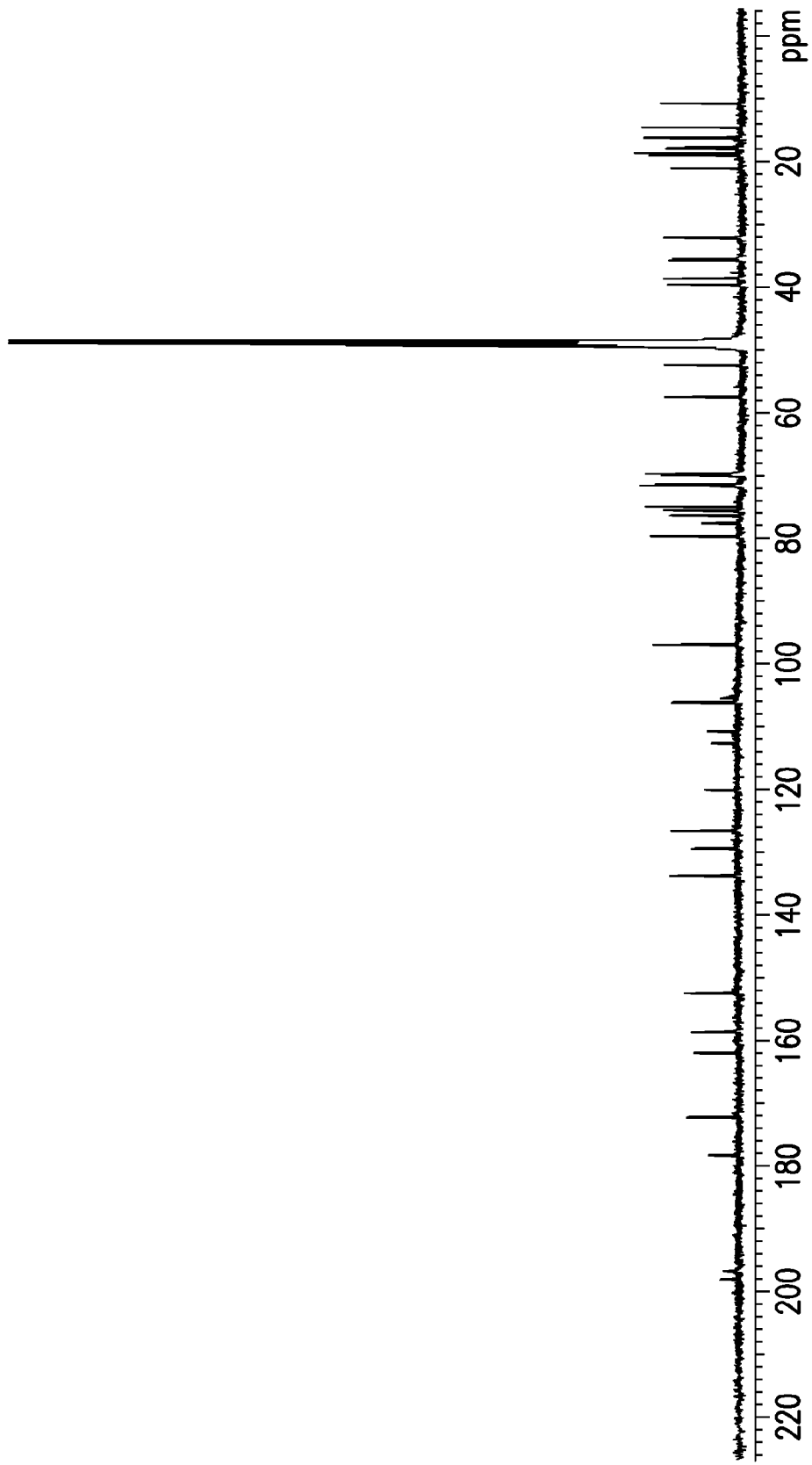
FIG. 1 is the $^{13}$C NMR spectrum of Compound A.

A first embodiment of the present invention relates to purified compounds selected from compounds of formula I:

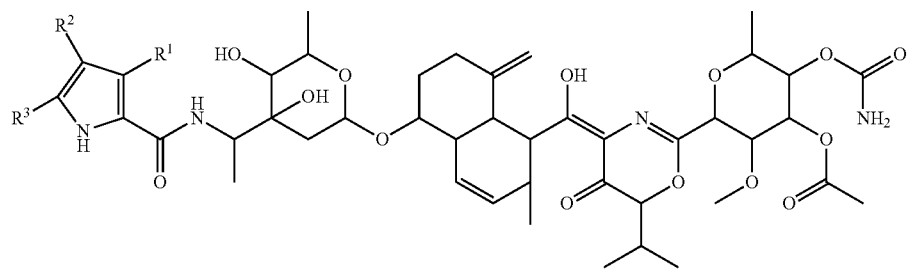

I and pharmaceutically acceptable salts thereof, wherein: $R^1$ and $R^2$ are independently selected from the group consisting of hydrogen and halogen; and $R^3$ is selected from the group consisting of hydrogen and $C_1$-$C_6$ alkyl. In all aspects of the embodiment, all other variables are as described above in the general formula.

A second embodiment of the present invention relates to purified compounds selected from compounds of formula II:

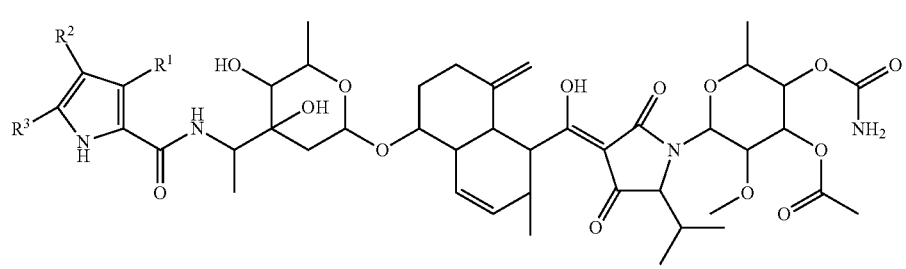

II and pharmaceutically acceptable salts thereof, wherein: $R^1$ and $R^2$ are independently selected from the group consisting of hydrogen and halogen; and $R^3$ is selected from the group consisting of hydrogen and $C_1$-$C_6$ alkyl. In all aspects of the embodiment, all other variables are as described above in the general formula.

In a third embodiment of the present invention, $R^1$ is selected from the group consisting of hydrogen and chlorine. In all aspects of the embodiment, all other variables are as described above in the general formula or in one or more of the first and second embodiments.

In a fourth embodiment of the present invention, $R^2$ is selected from the group consisting of hydrogen and chlorine. In all aspects of this embodiment, all other variables are as described above in the general formula or in one or more of the first through third embodiments.

In a fifth embodiment of the present invention, $R^3$ is selected from the group consisting of hydrogen, methyl and ethyl. In particular aspects of this embodiment, $R^3$ is selected from the group consisting of hydrogen and methyl. In all aspects of this embodiment, all other variables are as described above in the general formula or in one or more of the first through fourth embodiments.

In a sixth embodiment of the present invention, the purified compound is selected from the group consisting of:

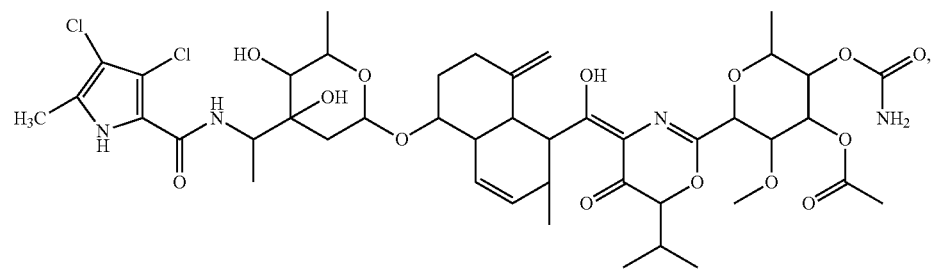

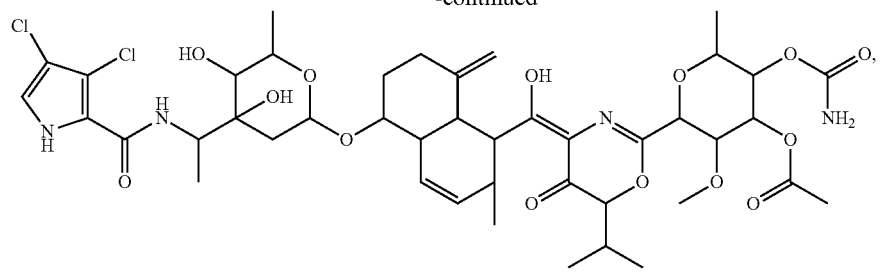
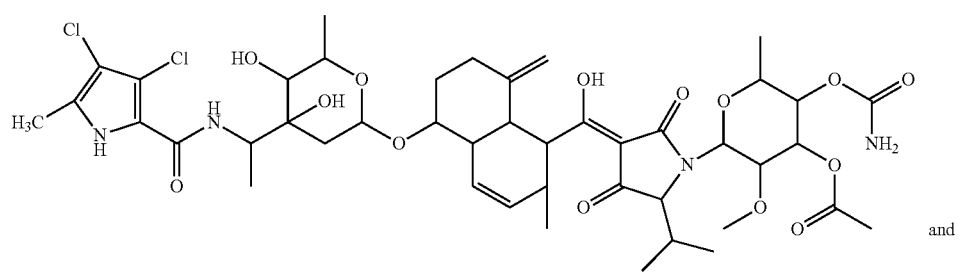
and
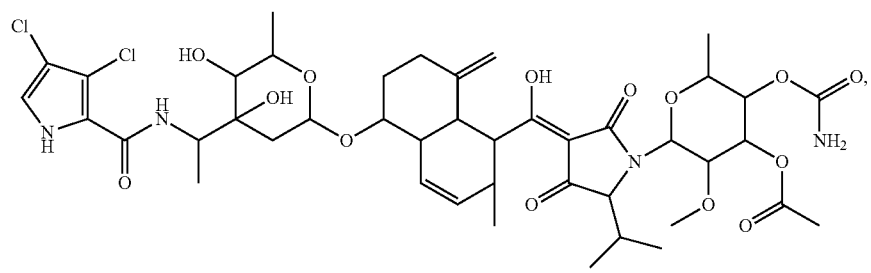
and pharmaceutically acceptable salts thereof.
In a first aspect of the sixth embodiment of the present invention, the purified compound is selected from the group consisting of
and pharmaceutically acceptable salts thereof. In a first instance of this first aspect, the purified compound is selected from the group consisting of
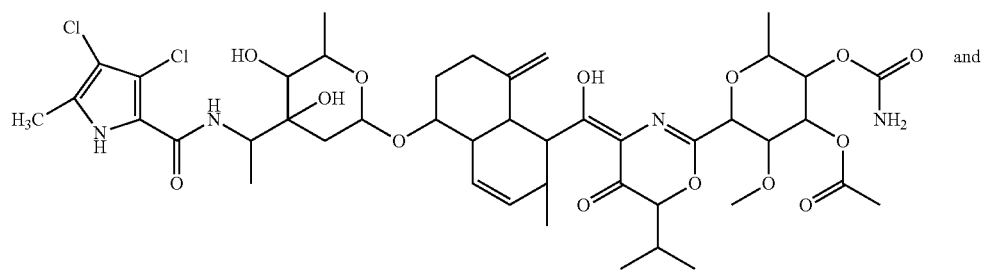
and
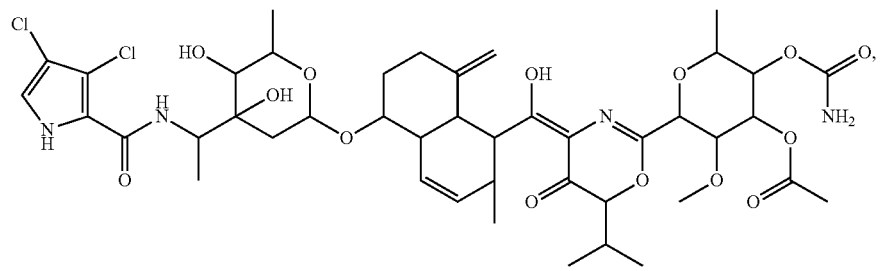

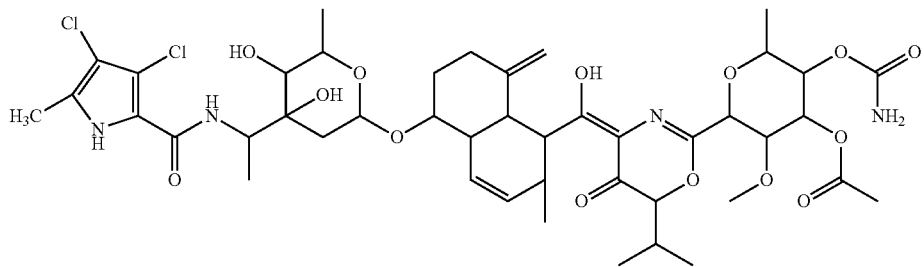

and pharmaceutically acceptable salts thereof. In a second instance of this first aspect, the purified compound is selected from the group consisting of

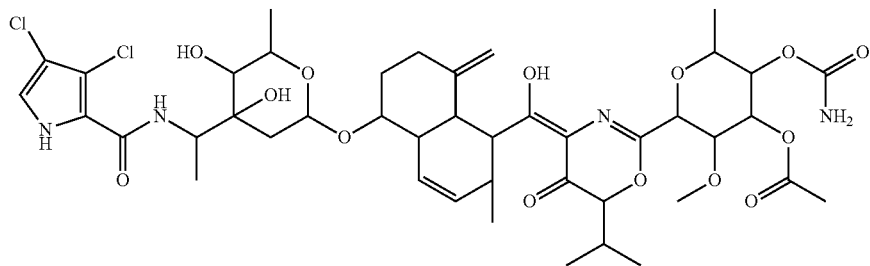

and pharmaceutically acceptable salts thereof.

In a second aspect of the sixth embodiment of the present invention, the purified compound is selected from the group consisting of

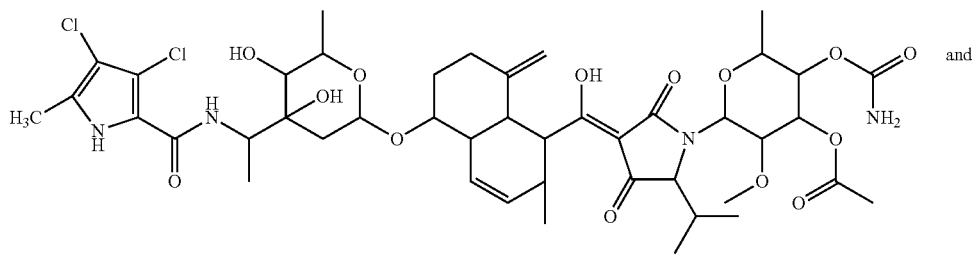

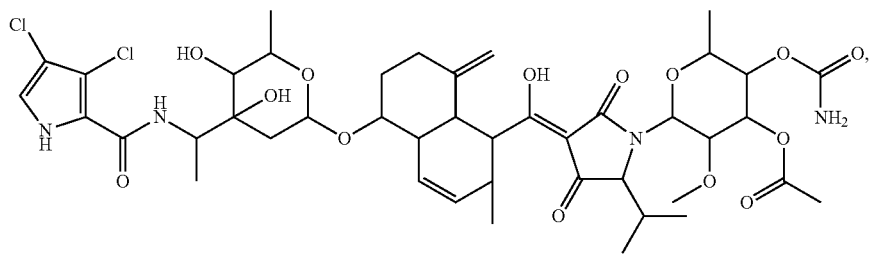

and pharmaceutically acceptable salts thereof. In a first instance of this second aspect, the purified compound is selected from the group consisting of

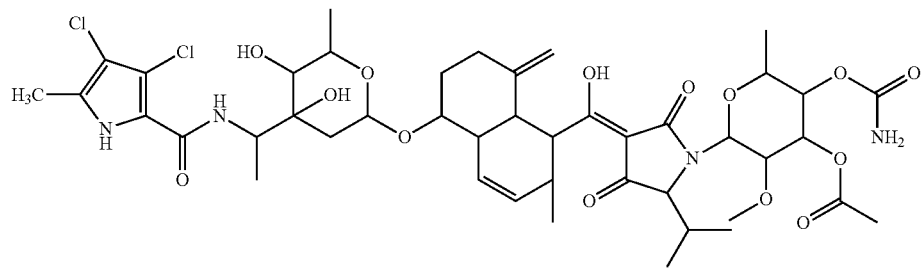

and pharmaceutically acceptable salts thereof. In a second instance of this second aspect, the purified compound is selected from the group consisting of

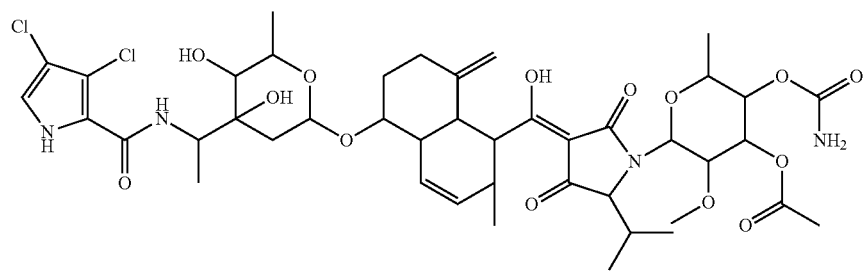

30 and pharmaceutically acceptable salts thereof.

A seventh embodiment of the present invention is directed to purified or partially purified bacterial extracts comprising one or more compounds as described above in the general formula or in one or more of the first through sixth embodiments.

Other embodiments of the present invention include the following:

(a) A pharmaceutical composition comprising one or more compounds as described above in the general formula or in one or more of the first through sixth embodiments and a pharmaceutically acceptable carrier.

(b) A method of inhibiting growth of bacteria, the method comprising treating with an effective amount of one or more compounds according to as described above in the general formula or in one or more of the first through sixth embodiments.

(c) A method of treating or preventing bacterial infection in a mammalian subject, the method comprising administering to the subject a therapeutically effective amount of one or more compounds as described above in the general formula or in one or more of the first through sixth embodiments.

(d) The method of (c), wherein said bacterial infection is caused by *Bacillus subtilis, Staphylococcus aureus, Staphylococcus epidermidis, Enterococcus faecalis, Enterococcus faecium, Escherichia coli, Streptococcus pneumoniae, Haemophilus influenzae*, or other bacteria, including *Staphylococcus hemolyticus, Streptococcus pyogenes, Pseudomonas aeruginosa, Acinetobacter calcoaceticus, Stenotrophomonas maltophilia* or *Clostridium difficile*.

(e) A method of controlling bacterial infection in a mammalian subject, the method comprising administering to the subject a therapeutically effective amount of one or more compounds as described above in the general formula or in one or more of the first through sixth embodiments.

(f) The method of (e), wherein said bacterial infection is caused by *Bacillus subtilis, Staphylococcus aureus, Staphylococcus epidermidis, Enterococcus faecalis, Enterococcus faecium, Escherichia coli, Streptococcus pneumoniae, Haemophilus influenzae*, or other bacteria, including *Staphylococcus hemolyticus, Streptococcus pyogenes, Pseudomonas aeruginosa, Acinetobacter calcoaceticus, Stenotrophomonas maltophilia* or *Clostridium difficile*.

(g) A biologically pure culture of a bacterial strain of the family Pseudonocardiaceae, genus *Kibdelosporangium* sp. (MA7385) deposited with the American Type Culture Collection as ATCC Patent Deposit Designation PTA-10354, or a biologically pure culture derived therefrom.

(h) A process of preparing the composition as described above in the sixth embodiment, the process comprising culturing and fermenting a culture of a bacterial strain of the family Pseudonocardiaceae, genus *Kibdelosporangium* sp. (MA7385) deposited with the American Type Culture Collection as ATCC Patent Deposit Designation PTA-10354, or a biologically pure culture derived therefrom.

The present invention also includes a compound of the present invention (i) for use in, (ii) for use as a medicament for, or (iii) for use in the preparation of a medicament for: (a) inhibiting bacterial growth or (b) preventing or treating infection by bacteria. In these uses, the compounds of the present invention can optionally be employed in combination with at least one additional, independently selected therapeutic agent selected from clinically useful agents, such as from beta-lactams, quinolones, oxazolidinones, vancomycin, sulfa drugs and daptomycin.

Additional embodiments of the invention include the pharmaceutical compositions, combinations and methods set forth in (a) through (h) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt as appropriate.

In the embodiments provided above, it is to be understood that the compounds of Formula I and Formula II may be provided in the form of a free base, a free acid or a pharmaceutically acceptable salt, or as a hydrate or a solvate of the compounds of Formula I and Formula II, to the extent that such free base, free acid, pharmaceutically acceptable salt, hydrate or solvate provides a stable compound and is consistent with the description of the embodiments. Thus, any reference to a "compound of Formula I" and/or "compound of Formula II" herein includes reference to the free base form or free acid form, as well as to any pharmaceutically acceptable salts, hydrates or solvates, provided that these forms represent stable compounds and are consistent with the description of the embodiments. It is also to be understood that each embodiment may be combined with one or more other embodiments, to the extent that such a combination provides a stable compound and is consistent with the description of the embodiments, even if not specifically set forth or recited. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

It is further to be understood that the embodiments of compositions and methods provided as (a) through (h) above are understood to include all embodiments of the compounds, including such embodiments as result from combinations of embodiments.

As used herein, unless otherwise noted, the following terms have the indicated meanings.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and tert-butyl, n- and isopropyl, ethyl and methyl. As another example, "$C_{1-4}$ alkyl" refers to n-, iso-, sec- and tert-butyl, n- and isopropyl, ethyl and methyl.

The terms "halogen", "halogen atom" and "halo" refer to fluorine, chlorine, bromine and iodine (alternatively referred to as fluoro, chloro, bromo, and iodo).

As a result of the selection of substituents and substituent patterns, certain of the compounds of the present invention can have asymmetric centers and can occur as mixtures of stereoisomers, or as individual diastereomers, or enantiomers. All isomeric forms of the claimed compounds, whether isolated or in mixtures, are within the scope of the present invention.

In the compounds of Formula I and Formula II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and Formula II. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I and Formula II can be prepared without undue experimentation by conventional techniques well known to those skilled in the art or by processes analogous to those described in the Examples herein using appropriate isotopically-enriched reagents and/or intermediates.

As would be recognized by one of ordinary skill in the art, certain of the compounds of the present invention can exist as tautomers. For the purposes of the present invention a reference to a compound of Formula I and Formula II is a reference to the compound per se, or to any one of its tautomers per se, or to mixtures of two or more tautomers.

As used herein, the term "composition" is intended to encompass a product comprising the specified ingredients, as well as any product that results, directly or indirectly, from combining the specified ingredients.

Compounds of the invention may be obtained from biological samples, as described below, may be produced by chemical modification of compounds obtained from biological samples, or may be synthesized chemically. The compounds of the invention may be provided as naturally occurring compounds and mixtures of compounds, or may be isolated and purified to produce "purified" compounds. The compounds of the invention may be provided as compositions containing naturally occurring compounds and mixtures of compounds, or may be isolated and purified to produce "purified" compositions.

As used herein, the term "purified" refers to compounds or compositions in an environment lacking in one or more components normally associated with the desired compounds of Formula I and Formula II in their original or natural state. Reference to "purified" refers to the environment of the compound and does not necessarily require purification. Purified compounds or compositions can be produced, for example, through isolation from a producing strain, through synthetic means, through purification steps or through a combination of means. For example, a composition comprising a mixture of compounds of Formula I and Formula II may be referred to as a "purified" composition if provided in a form substantially lacking in any fermentation components other than the claimed mixture. Similarly, a composition isolated from a biologically pure sample of a bacterial strain may be a "purified" composition if one or more components are removed by an isolation or purification process. In embodiments, "purified" may refer to compounds or compositions that have 50%-99% purity as defined as the percentage of the mass of the desired compounds or compositions relative to the total mass present. In particular embodiments, compounds or compositions may have 50% purity, 60% purity, 75% purity, 90% purity, 95% purity, 98% purity or 99% purity.

As used herein, the term "biologically pure sample" of a bacterial strain refers to a sample of the bacterial strain of interest that is provided in a form not found in nature; that is, a biologically pure sample of a bacterial strain contains the bacterial strain of interest but is substantially lacking in bacterial strains, bacterial materials and/or other biological materials.

The term "subject" (alternatively referred to herein as "patient") as used herein refers to an animal, preferably a mammal that has been the object of treatment, observation or experiment. The term "mammal" as used herein is intended to include most preferably humans, as well as warm-blooded animals, including domesticated animals such as cats, dogs, livestock, and the like.

The compounds of Formula I and Formula II and pharmaceutically acceptable salts thereof, also called "active ingredients" herein, are most effectively utilized when formulated into compositions or formulations with a pharmaceutically acceptable carrier, according to conventional pharmaceutical compounding techniques. The term "composition," as in "pharmaceutical composition," is intended to encompass products that comprise one or more active ingredient(s) and inert ingredient(s) that make up the carrier. The term "composition" is also intended to encompass any products that result, directly or indirectly, from combination, complexation, aggregation or other interactions of any two or more active ingredient(s) and/or inert ingredient(s); any products that result, directly or indirectly, from the dissociation of one or more of the active ingredient(s) and/or inert ingredient(s); and any products that result from any other types of reactions of one or more of the active ingredient(s) and/or inert ingredient(s).

The pharmaceutical compositions contain at least a therapeutically effective antibiotic amount of active ingredient(s). A "therapeutically effective amount" as used herein refers to an amount of an active ingredient sufficient to produce a desired therapeutic effect. For example, a therapeutically effective antibiotic amount of a compound is an amount sufficient to demonstrate antibiotic activity and/or inhibit growth of one or more bacterial strains. Therapeutically effective antibacterial amounts of active ingredient(s) in pharmaceutical compositions may be provided in a range of about 10 mg of active ingredient(s) per kg of patient body weight to about 1000 mg active ingredient(s) per kg of patient body weight.

By "pharmaceutically acceptable" is meant that the ingredients of the pharmaceutical composition must be compatible with each other and not deleterious to the recipient thereof.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable pharmaceutically acceptable salts of the compounds of Formula I and Formula II include, for example, inorganic base salts, such as alkali metal salts (e.g., sodium and potassium salts), ammonium salts, and organic base salts. Suitable organic base salts include amine salts, such as tetra-alkyl-ammonium salts (e.g., tetrabutylammonium and trimethylcetylammonium), trialkylamine salts (e.g., triethylamine), dialkyl amine salts (dicyclohexylamine), optionally substituted benzylamines (e.g., phenylbenzylamine and para-bromobenzylamine), ethanolamine, diethanolamine, N-methylglucosamine, N-methylpiperidine, pyridine, substituted pyridines (e.g., collidine, lutidine and 4-dimethylaminopyridine), and tri(hydroxymethyl)methylamine salts; and amino acid salts (e.g., lysine or arginine salts).

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., agents useful for treating bacterial infection), "administration" and its variants are each understood to include concurrent and sequential provision of the compound, salt, hydrate or solvate, and other agents.

The term "effective amount" as used herein means an amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition whose likelihood of occurrence or severity is being reduced. The term also includes herein the amount of active compound sufficient to inhibit bacterial growth and thereby elicit the response being sought (i.e., an "inhibition effective amount"). When the active compound (i.e., active ingredient) is administered as the salt, references to the amount of active ingredient are to the free acid or free base form of the compound.

The pharmaceutical compositions may be prepared by intimately mixing one or more active ingredient(s) with a carrier, and the components of the carrier may be selected to provide the desired medium. For example, a formulated cream or lotion may be provided by mixing active ingredient(s) into appropriately selected cream or lotion components to provide an active ingredient(s) concentration of between about 0.01% and about 99%.

Pharmaceutical compositions according to aspects of the invention may be formulated as compositions suitable for oral, topical, parenteral (including intraperitoneal (I.P.), subcutaneous, intramuscular and intravenous (I.V.)), nasal and suppository administration, or for administration by insufflation.

For oral administration, pharmaceutical compositions of embodiments may be formulated as liquid or solid compositions. Liquid compositions may be prepared by combining the active ingredient(s) with pharmaceutically acceptable liquid carrier(s), such as water, glycols, oils, alcohols and the like. For solid compositions, the active ingredient(s) may be combined with pharmaceutically acceptable solid carrier(s), such as starches, sugars, kaolin, ethyl cellulose, calcium carbonate, sodium carbonate, calcium phosphate, talc and lactose. These solid carrier(s) may optionally be combined with a lubricant, such as calcium stearate, and/or with a binder-disintegrating agent or the like. Because tablets and capsules are easily administered, these dosage forms may represent the most advantageous oral-dosage form for some situations. Compositions in unit-dosage form also constitute an aspect of the invention.

For administration by injection, pharmaceutical compositions of embodiments may be formulated as suspensions, solutions or emulsions. The pharmaceutically acceptable carriers for injectible compositions may be oily vehicles or aqueous vehicles, such as 0.85% sodium chloride in water or 5% dextrose in water. In addition, injectible compositions may include formulating agents, such as buffering agents, solubilizing agents, suspending agents and/or dispersing agents. Buffering agents, as well as additives such as saline or glucose, may be added to make the solutions isotonic. For drip-intravenous administration, the active ingredient(s) may be solubilized in alcohol/propylene glycol or polyethylene glycol. Injectible compositions may be provided as liquid compositions, in unit-dosage form in ampoules or in multidose containers, optionally containing an added preservative. Alternatively, the active ingredient(s) may be provided in powder form, and may be reconstituted in a suitable liquid vehicle prior to administration.

The term "unit-dosage form," as used in the specification and claims, refers to physically discrete units, each containing a predetermined quantity of active ingredient(s), calculated to produce a desired therapeutic effect, in association with an acceptable carrier. Examples of such unit-dosage forms include tablets, capsules, pills, powder packets, wafers, measured units in ampoules or in multidose containers, and the like.

Compounds described herein may be prepared by fermentation of a bacterial strain of the family Pseudonocardiaceae, genus *Kibdelosporangium* sp. (MA7385), or bacterial strains derived therefrom and biologically pure cultures of bacterial strains derived therefrom, and solvent extraction. In particular, compounds of the invention may be prepared by fermentation of *Kibdelosporangium* sp. (MA7385) or of progeny, descendant or mutant bacterial strains of *Kibdelosporangium* sp. (MA7385). In embodiments, compounds obtained by fermentation of bacterial strains and solvent extraction may be further synthetically modified to yield additional compounds of the invention. Additionally, compounds of the invention may be prepared synthetically.

*Kibdelosporangium* sp. (MA7385) was preliminarily identified as a *Streptomyces* strain but has been confirmed to be a *Kibdelosporangium* strain, which was isolated from a soil sample collected in a forest of the Central African Republic. The *Kibdelosporangium* sp. (MA7385) been deposited under the Budapest Treaty, in the culture collection of the American Type Culture Collection at 10801 University Boulevard, Manassas, Va. 20110-2209 on Sep. 23, 2009, and was assigned ATCC Patent Deposit Designation PTA-10354.

EXAMPLES

Example 1

Fermentation Procedure

Fermentation of *Kibdelosporangium* sp. (MA7385) was accomplished by inoculating several agar plugs with mycelia into a seed broth flask (50 mL medium in 250 mL baffled flask). The formulation for the seed broth is a follows (gm per liter, unless specified):

| | |
|---|---|
| Soluble Starch | 20.0 |
| Dextrose | 10.0 |
| NZ Amine type E | 5.0 |
| Beef Extract | 3.0 |
| Peptone | 5.0 |
| Yeast Extract | 5.0 |
| CaCO$_3$ | 1.0 |
| distilled H$_2$O | to 1 Liter |

The pH is adjusted to 7.0 with NaOH prior to addition of CaCO$_3$. The flasks were incubated at 28° C., 80% relative humidity and shaken on a rotary shaker at 220 rpm.

When the seed stage flasks have grown for 3 days, a 1 mL aliquot is used to inoculate each flask of FR23 production medium (50 mL medium in a 250 unbaffled flask). The formulation consists of (gm per liter):

| | |
|---|---|
| Glucose | 5.0 |
| Soluble Starch | 30.0 |
| Cane Molasses | 20.0 |
| Pharmamedia | 20.0 |
| distilled H$_2$O | to 1 Liter |

The pH was adjusted to 7.0 with NaOH prior to sterilization. The flasks were incubated at 28° C., 80% relative humidity on a rotary shaker at 220 rpm for 7 days.

Isolation Procedure

A 12 L fermentation broth was extracted with 12 L acetone by shaking at a reciprocating shaker for more than 1 hour. The mycelial content was filtered through CELITE, and the filtrate was concentrated under reduced pressure to remove most of acetone. The aqueous extract (12 L) was extracted three times with 12 L each of methyl ethyl ketone (MEK). MEK extracts were combined and concentrated under reduced pressure to dryness yielding a gum, which was dissolved in small volume of methanol (~20 mL) and chromatographed on a 450 cc SEPHADEX LH 20 column. The column was eluted with methanol, and the fractions containing the compounds were pooled and concentrated under reduced pressure to dryness. One-third portion of the LH20 fraction was dissolved in minimum volume of methanol and diluted with methylene chloride to a ratio of 90 parts methylene chloride to 10 parts methanol. This solution was then charged on a 35 cc (10 g) silica gel cartridge and washed with 3-4 column volumes with 10, 20, 30% methanol in methylene chloride. The compounds of interest eluted in 10-20% methanol fraction. This process was repeated twice with rest of the material, and pooled fractions from three columns were concentrated under reduced pressure to yield a brown gum. The enriched material from silica gel was dissolved in 10 mL methanol. One-fifth (2 mL) was chromatographed on an one-inch reversed phase PRP-1 (Hamilton's pH stable HPLC column, 250×21.5 mm) using gradient elution with methanol:0.25M sodium phosphate buffer (pH 7) 60:40 to 80:20 in 40 minutes at a flow rate of 10 mL/min. The chromatography was repeated with rest of the material four times. Fractions eluting at 35-38, 39-40 and 41-44 from each of the five chromatographic runs were pooled. These fractions were triturated with 4-6 mL methanol three times. The solution contained the compound, leaving behind most of the buffer as a solid. The methanol solution from fractions 35-38 and 41-44 were concentrated and rechromatographed on a ZORBAX RX C8 (250×21.5 mm) column and eluted with a 50 minute linear gradient of 50-100% aqueous methanol. The major components from each chromatography were lyophilized to give the following compositions as colorless powders.

Composition A

Compound A-I of Formula I

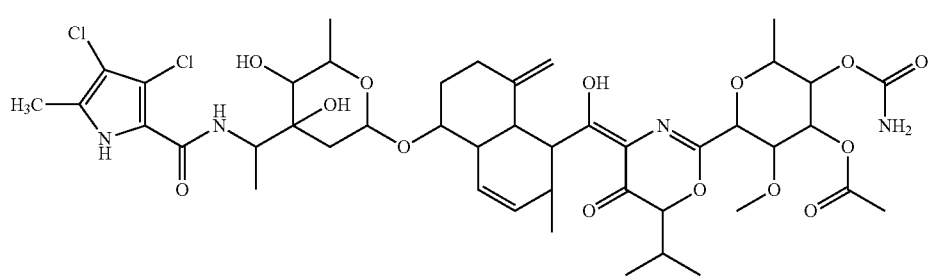

3-O-acetyl-1,5-anhydro-4-O-carbamoyl-6-deoxy-1-[(4Z)-4-[(5-{[2,6-dideoxy-3-C-(1-{[(3,4-dichloro-5-methyl-1H-pyrrol-2-yl)carbonyl]amino}ethyl)hexopyranosyl]oxy}-2-methyl-8-methylidene-1,2,4a,5,6,7,8,8a-octahydronaphthalen-1-yl)(hydroxy)methylidene]-5-oxo-6-(propan-2-yl)-5,6-dihydro-4H-1,3-oxazin-2-yl]-2-O-methylhexitol.

Compound A-II of Formula II

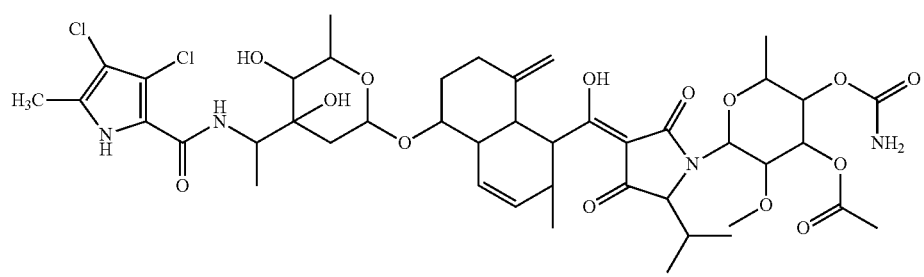

A-II

5-[(Z)-[1-(3-O-acetyl-4-O-carbamoyl-6-deoxy-2-O-methylhexopyranosyl)-2,4-dioxo-5-(propan-2-yl)pyrrolidin-3-ylidene](hydroxy)methyl]-6-methyl-4-methylidene-1,2,3,4,4a,5,6,8a-octahydronaphthalen-1-yl-2,6-dideoxy-3-C-(1-{[(3,4-dichloro-5-methyl-1H-pyrrol-2-yl)carbonyl]amino}ethyl)hexopyranoside.

Physical properties of Composition A were determined as follows:

FIG. 1 is the carbon-13 ($^{13}$C) nuclear magnetic resonance (NMR) spectrum of Composition A; characteristic peaks are observed as summarized in Table 1. The $^{13}$C NMR spectra were collected on either a VARIAN INOVA 500 or 600 MHz spectrometer, operating at either 125 or 150 MHz for $^{13}$C nuclei. The chemical shifts were referenced to residual CD$_3$OD ($\delta_C$ 49.0 ppm). Data were collected uniformly at 25° C. in 3 mm NMR tubes. A NORLAC 3 mm H{CN} indirect Z-gradient probe was used for all samples. VARIAN standard pulse sequences were used for all data collection.

Figure 2:
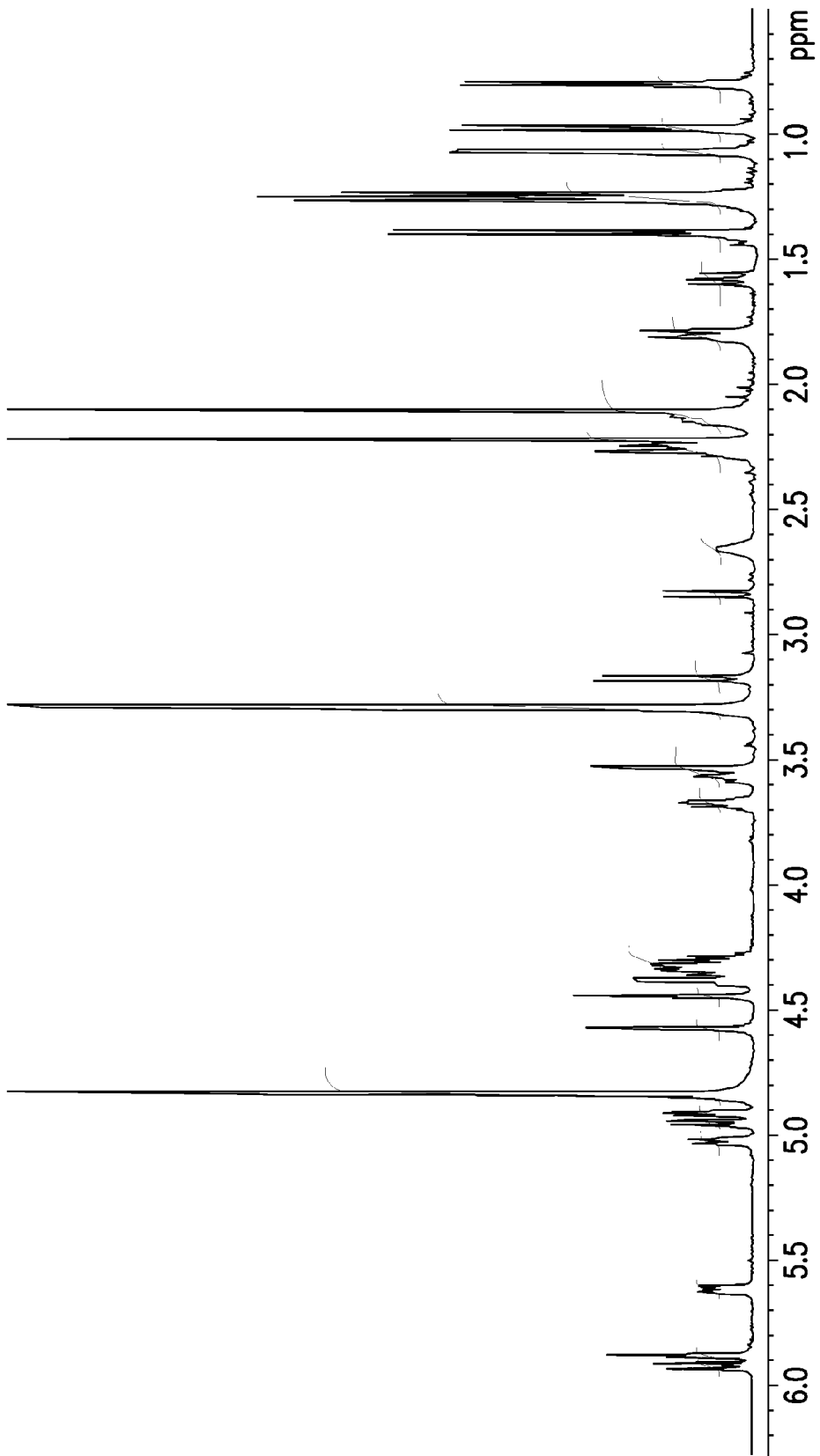
FIG. 2 is the $^1$H NMR spectrum of Compound A.

FIG. 2 is the $^1$H NMR spectrum of Composition A; characteristic peaks are observed as summarized in Table 1. The $^1$H NMR spectra were collected on either a VARIAN INOVA 500 or 600 MHz spectrometer, operating at either 500 or 600 MHz for $^1$H nuclei. The chemical shifts were referenced to residual CHD$_2$OD ($\delta_H$ 3.30 ppm). Data were collected uniformly at 25° C. in 3 mm NMR tubes. A NORLAC 3 mm H{CN} indirect Z-gradient probe was used for all samples. VARIAN standard pulse sequences were used for all data collection.

The ultraviolet (UV) absorption spectrum of Composition A, taken in MeOH, exhibited characteristic absorption bands of $\lambda_{max}$ (log $\epsilon$)=248 nm (sh) and 276 nm (4.42). The UV spectrum was recorded on a PERKIN ELMER LAMBDA 35 UV/Vis spectrometer.

The infrared (IR) absorption spectrum of Composition A, taken using ZnSe, exhibited characteristic absorption bands of $\nu_{max}$=3417, 2932, 1732, 1611, 1537, 1454, 1376, 1313, 1233, 1159, 1079, 1004, 893, 830, 789, 745 cm$^{-1}$. IR spectral data was obtained using a PERKIN ELMER SPECTRUM ONE spectrometer by transferring a small aliquot of Composition A, dissolved in methanol, onto a ZnSe plate.

The high-resolution mass spectrum of Composition A produced HRESIFTMS (m/z): observed for M+H=939.3562, calculated for C$_{44}$H$_{60}$Cl$_2$N$_4$O$_{14}$$^+$H=939.3561. High-resolution mass spectra were obtained on a THERMO FINNIGAN LTQ-FT spectrometer, using electrospray ionization and a FINNIGAN ION MAX source with source fragmentation on and equal to 18 volts.

Composition B
Compound B-I of Formula I

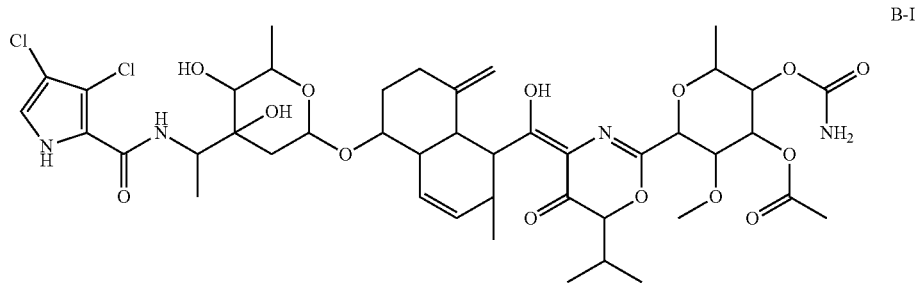

B-I

3-O-acetyl-1,5-anhydro-4-O-carbamoyl-6-deoxy-1-[(4Z)-4-[(5-{[2,6-dideoxy-3-C-(1-{[(3,4-dichloro-1H-pyrrol-2-yl)carbonyl]amino}ethyl)hexopyranosyl]oxy}-2-methyl-8-methylidene-1,2,4a,5,6,7,8,8a-octahydronaphthalen-1-yl)(hydroxy)methylidene]-5-oxo-6-(propan-2-yl)-5,6-dihydro-4H-1,3-oxazin-2-yl]-2-O-methylhexitol.

Compound B-II of Formula II

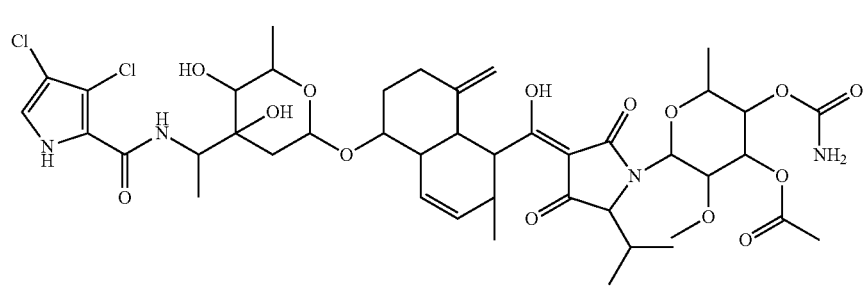

B-II

5-[(Z)-[1-(3-O-acetyl-4-O-carbamoyl-6-deoxy-2-O-methylhexopyranosyl)-2,4-dioxo-5-(propan-2-yl)pyrrolidin-3-ylidene](hydroxy)methyl]-6-methyl-4-methylidene-1,2,3,4,4a,5,6,8a-octahydronaphthalen-1-yl 2,6-dideoxy-3-C-(1-{[(3,4-dichloro-1H-pyrrol-2-yl)carbonyl]amino}ethyl)hexopyranoside.

Figure 3:
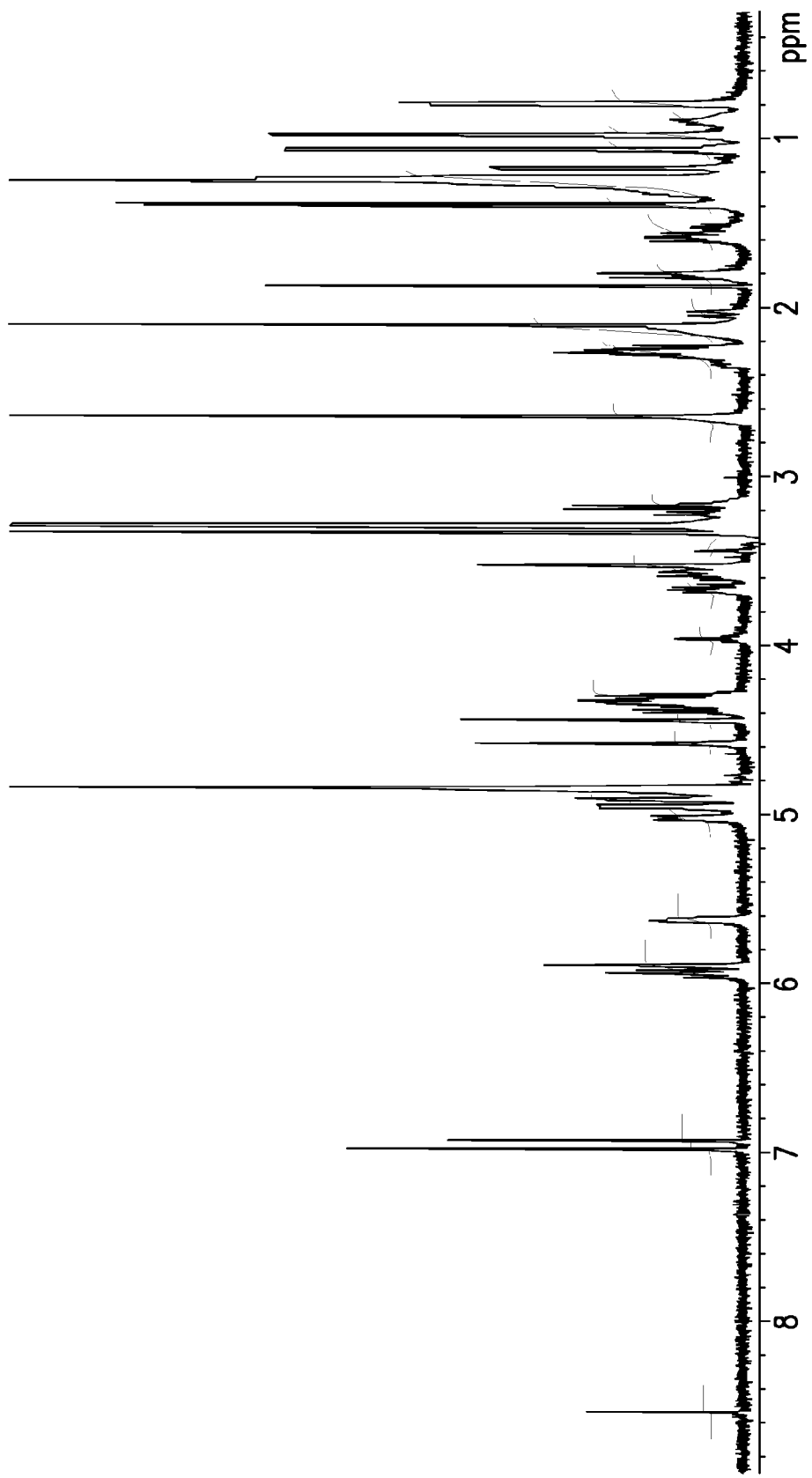
FIG. 3 is the $^1$H NMR spectrum of Compound B.

FIG. 3 is the $^1$H NMR spectrum of Composition B; characteristic peaks are observed as summarized in Table 1. The $^1$H NMR spectra were collected on either a VARIAN INOVA 500 or 600 MHz spectrometer, operating at either 500 or 600 MHz for $^1$H nuclei. The chemical shifts were referenced to residual CHD$_2$OD ($\delta_H$ 3.30 ppm). Data were collected uniformly at 25° C. in 3 mm NMR tubes. A NORLAC 3 mm H{CN} indirect Z-gradient probe was used for all samples. VARIAN standard pulse sequences were used for all data collection.

The high-resolution mass spectrum of Composition B produced HRESIFTMS (m/z): observed M+H=925.3410, calculated for $C_{43}H_{58}Cl_2N_4O_{14}{}^+$H=925.3405. High-resolution mass spectra were obtained on a THERMO FINNIGAN LTQ-FT spectrometer, using electrospray ionization and a FINNIGAN ION MAX source with source fragmentation on and equal to 18 volts.

TABLE 1

$^{13}$C and $^1$H NMR spectral data

| Type | Composition A $^{13}$C | Composition A $^1$H | Composition B $^1$H |
|---|---|---|---|
| C.° | 152.2 | | |
| CH$_2$ | 35.6 | 2.26, m (eq) | 2.26, m |
| | | 2.12, m (ax) | 2.15, m |
| CH$_2$ | 35.3 | 2.25, m (eq) | 2.25, m |
| | | 1.26, m (ax) | 1.28, m |
| CH | 79.6 | 3.56, dt, 4, 11 | 3.56, m |
| CH | 49.9 | 1.82, dt, 2.5, 11 | 1.79, m |
| CH | 126.5 | 5.92, dt, 10, 2 | 5.93, dt, 10, 2. |
| CH | 133.7 | 5.62, ddd, 10, 4.5, 3 | 5.62, ddd, 10, 4.5, 3 |
| CH | 32.1 | 2.65, m | 2.65, brm |
| CH | 48.0 br | 4.33, m | 4.36, m |
| CH | 39.5 | 2.26, m | 2.26, m |
| C.° | 198.0 br | | |
| C.° | 105.2 br | | |
| C.° | 196.6 br | | |
| CH | 69.7 br | 3.52, d, 2.5 | 3.52, d, 2.5 |
| CH | 32.0 br | 2.14, m | 2.15, m |
| CH$_3$ | 17.8 | 0.97, d, 7 | 0.98, d, 7 |
| CH$_3$ | 17.7 | 1.07, d, 7 | 1.07, d, 7 |
| CH$_2$ | 106.1 | 4.57, s | 4.58, brs |
| | | 4.44, s | 4.44, brs |
| CH$_3$ | 18.9 | 0.80, d, 7 | 0.80, d, 7.5 |
| C | 178.1 br | | |
| CH | 77.5 br | 5.02, brd, 9 | 5.01, brd, 9.5 |
| CH | 75.6 | 4.33, m | 4.33, m |
| CH | 69.9 | 5.88, t, 3 | 5.89, t, 3 |
| CH | 69.8 | 4.91, dd, 6, 3 | 4.91, dd, 6, 3.5 |
| CH | 71.4 | 4.30, pent, 7 | 4.30, pent, 7 |
| CH$_3$ | 14.5 | 1.39, d, 7 | 1.39, d, 7 |
| CH | 96.8 | 4.94, dd, 10, 2 | 4.95, brd, 10 |
| CH$_2$ | 38.5 | 1.79, dd, 13.5, 2 (eq) | 1.80, brd, 13.5 |
| | | 1.57, dd, 13.5, 10 (ax) | 1.58, dd, 13.5, 9.5 |
| C.° | 76.4 | | |
| CH | 74.9 | 3.17, d, 9 | 3.18, d, 9 |
| CH | 71.7 | 3.67, dq, 9, 6 | 3.67, dd, 9, 6 |
| CH$_3$ | 18.5 | 1.26, d, 6 | 1.27, d, 6 |
| CH | 52.4 | 4.37, q, 7 | 4.38, q, 6.5 |
| CH$_3$ | 16.2 | 1.24, d, 7 | 1.25, d, 7 |
| C.° | 161.7 | | |
| C.° | 120.0 | | |
| C.° | 112.4 | | |
| C.° | 110.6 | | |
| C.° | 129.4 | | 6.98, s |
| CH$_3$ | 10.8 | 2.21, s | |
| C.° | 158.4 | | |
| C.° | 172.0 | | |
| CH$_3$ | 21.0 | 2.11, s | 2.10, s |
| CH$_3$ | 57.5 | 3.28, s | 3.34, s |

Example 2

Composition A was tested for antibacterial activity against strains of *Bacillus subtilis, Staphylococcus aureus, Enterococcus faecalis, Escherichia coli, Streptococcus pneumoniae* and *Haemophilus influenzae*, and compositions A and B were tested against a control of *Candida albicans*. Composition B was tested for antibacterial activity against *Staphylococcus aureus* strains.

Media & Media Preparation

The following materials were used in the testing of Compositions A and B: MIC SABOURAUD DEXTROSE AGAR PLATES (BBL); MICROBANK Beads (KRAMER SCIENTIFIC); 2000 MICROTITER plate inoculator; 96-Well MICROTITER plates, lids, inoculum trays (DYNEX LABORATORIES); and 8-CHANNEL FINN MULTICHANNEL pipettor, 0.5-10 µL volume. All agar plates were received prepared from manufacturer.

The following media were used in the testing of Compositions A and B: CATION-ADJUSTED MUELLER HINTON BROTH (MH; BBL); 50% Lysed Horse Blood (LHB; BBL) (stored frozen); RPMI 1640 (BIOWHITTAKER); Human Serum (PEL-FREEZ); RPMI 1640 (BIOWHITTAKER); *Haemophilus* Test Medium (HTM, REMEL); TRYPTICASE Soy Broth (TSB, 5 mL/tube; BBL); 0.9% Sodium Chloride (Saline; BAXTER); TRYPTICASE Soy+5% Sheep Blood Agar Plates (TSA; BBL); Chocolate Agar Plates (BBL); 2× Skim Milk (REMEL); and 2× TRYPTICASE Soy Broth (TSB, BBL)+15% glycerol/50% horse serum. The media were prepared as follows:

CATION-ADJUSTED MUELLER HINTON BROTH: Prepared according to manufacturer's instructions (22 g dissolved in 1000 mL water; autoclaved 22 minutes). Stored refrigerated. Filter-sterilized before use using a CORNING 0.45 Tm cellulose acetate filter.

50% Lysed Horse Blood: Defibrinated horse blood is diluted 1:1 with sterile distilled water; frozen, thawed and re-frozen (at least 7 times), then centrifuged. Stored frozen at −20° C.

CATION-ADJUSTED MUELLER HINTON+2.5% Lysed Horse Blood: Aseptically add 5 mL 50% lysed horse blood to 100 mL CATION-ADJUSTED MUELLER HINTON BROTH. Filter-sterilize before use using a CORNING 0.45 Tm cellulose acetate filter.

CATION-ADJUSTED MUELLER HINTON+50% Human Serum: Aseptically add 50 mL Human Serum to 50 mL 2× CATION-ADJUSTED MUELLER HINTON BROTH. Filter-sterilize before use using a CORNING 0.45 Tm cellulose acetate filter.

Haemophilus Test Medium: Received prepared from manufacturer. Filter-sterilized before use using a CORNING 0.45 Tm cellulose acetate filter.

0.9% Sodium Chloride: Received prepared from manufacturer.

2× Skim Milk: Received prepared from manufacturer.

Selection and Maintenance of Isolates

The strains used are isolates from the Merck Culture Collection; these culture are maintained as frozen stocks at −80° C. in a) MICROBANK beads or b) 2× TRYPTICASE Soy Broth+15% glycerol/50% horse serum. In particular, the strains were as follows.

The *Bacillus subtilis* strain used was obtained from the Merck Culture Collection, and is identified as MB964. The culture was maintained frozen at −80° C. in MICROBANK beads.

The *Staphylococcus aureus* strains used were obtained from the Merck Culture Collection, and are identified as MB2865 and MB5957. The culture was maintained frozen at −80° C. in MICROBANK beads.

The *Enterococcus faecalis* strain used was obtained from the Merck Culture Collection, and is identified as CL8516. The culture was maintained frozen at −80° C. in MICROBANK beads.

The *Escherichia coli* envA1 tolC strain used was a cell-wall permeable strain obtained from the Merck Culture Collection, and is identified as MB5746. The culture was maintained frozen at −80° C. in MICROBANK beads.

The *Streptococcus pneumoniae* strain used was obtained from the Merck Culture Collection, and is identified as CL2883. The culture was maintained frozen at −80° C. in 2× Trypticase Soy Broth+15% glycerol/50% horse serum.

The *Haemophilus influenzae* strain used was obtained from the Merck Culture Collection, and is identified as MB4572. The culture was maintained frozen at −80° C. in 2× Trypticase Soy Broth+15% glycerol/50% horse serum. The strain of *Haemophilus influenzae* is a mouse pathogen used for in vivo testing at Merck.

The *Candida albicans* control strain used was obtained from the Merck Culture Collection, and is identified as MY1055. The culture was maintained frozen at −80° C. in MICROBANK beads.

Inoculum Preparation

Selected isolates were subcultured onto either TRYPTICASE Soy+5% Sheep Blood Agar Plates (*Bacillus subtilis, Staphylococcus aureus, Enterococcus faecalis, Escherichia coli* and *Streptococcus pneumoniae*), Chocolate Agar Plates (*Haemophilus influenzae*) or Sabouraud Dextrose Agar (*Candida*) and incubated at 35° C. *Streptococcus pneumoniae* and *Haemophilus* were incubated in 5% $CO_2$; all other isolates were incubated in ambient air. Isolates were subcultured twice before assay.

Colonies were selected from plates and used to prepare an inoculum having a density equivalent to a 0.5 McFarland standard in TRYPTICASE Soy Broth; an inoculum with a density equivalent to a 1.0 McFarland standard was prepared for *Streptococcus pneumoniae*. The inoculum density for all cultures was ~$10^8$ CFU/mL in TSB. This TSB inoculum was diluted 1:10 in sterile saline (4 mL inoculum+36 mL saline; equivalent to ~$10^7$ CFU/mL) and kept on ice until used to inoculate microtiter plates.

Plate Filling

Drug Stock Solutions and Dilutions

Test plates were prepared for each strain as follows. To each well of a 96-well plate (with columns 1-12 and rows A-H), 100 μL of appropriate test medium (*Bacillus subtilis, Staphylococcus aureus, Enterococcus faecalis, Escherichia coli*—CATION-ADJUSTED MUELLER HINTON BROTH plates; *Streptococcus pneumoniae*—CATION-ADJUSTED MUELLER HINTON BROTH+5% Lysed Horse Blood plates; *Haemophilus influenzae*—Haemophilus test media plates; *Candida albicans*—RPMI 1640) was added using the Thermal-LabSystems MULTIDROP™ dispenser. The Clinical Laboratory Standards Institute (CLSI) (formerly National Committee for Clinical Laboratory Standards (NCCLS)) formula was used to calculate the amount of dilution needed for a standard solution.

Composition Preparation

The test compositions were prepared on a weight basis. The test compositions were prepared to 2 mg/mL in 100% DMSO, then diluted to 1 mg/mL in a 1:1 dilution of DMSO/2×CAMHB (final concentration=50% DMSO/50% CAMHB). The test compositions were serially diluted 1:1 in 50% DMSO/50% CAMHB in BD Biosciences Deep Well Polypropylene 96-well plates (starting concentration 1 mg/mL) as follows:

To the first well of each row, 100 μL of the compound stock solutions (1 mg/mL) were added with multichannel Matrix pipette. Compounds were serially diluted two-fold with Perkin Elmer CETUS PRO/PETTE™ diluter or TECAN™ (100 μL taken from first well of each row and placed into second well and mixed, 100 μL of second well of each row taken and placed into third well and mixed, etc.) across the plate to column 11 (column 12 was the growth control well-no drug), and the last 100 μL was discarded, yielding compound concentrations of 64-0.00004 μg/mL. Penicillin G and Clarithromycin, the control compounds, were prepared as a stock solution of 10 mg/mL in DMSO and prepared in micro-titer plate as stated above for test compounds. Ciprofloxacin was included as a control for the serum protein binding assay.

Microbroth Dilution Assay

Using a FINN AUTOMATED MULTICHANNEL PIPETTE, (0.5-10 μL volume) 6.4 μL of test solutions were added to wells of filled microtiter plates (concentration of antimicrobial in first well=64 μg/mL; concentration of DMSO 3.2%). Antimicrobials were added in this manner to keep constant the amount of DMSO in each well (to keep compounds solubilized and to account for the possibility of non-specific killing by the DMSO. The last row contained a growth control of 3.2% DMSO.

Plate Inoculation and Activity Determination

All wells of microtiter plates were inoculated with (saline-diluted) culture using the MIC 2000 System, an automated plate inoculating device that delivered an inoculum of 1.5 TL per well. Plates are incubated at 35° C. in ambient air. An uninoculated plate was also incubated as a sterility check. Results were recorded after 18-24-hours' incubation. Plates were read to no growth.

The minimum inhibitory concentration (MIC-100) for all compounds was determined to be the lowest concentration of compound at which there was no visible growth as compared to growth control without drug, as determined after an incubation period of 22 to 24 hours. MICs were obtained in accordance to the CLSI guidelines.

Composition A demonstrated antibacterial activity against various strains of Bacillus subtilis, Staphylococcus aureus, Enterococcus faecalis, Escherichia coli, Streptococcus pneumoniae and Haemophilus influenzae. Composition B demonstrated antibacterial activity against various strains of Staphylococcus aureus. Minimum inhibitory concentration (MIC) values, which ranged from 0.1 to 64 µg/mL, were observed for Compositions A and B as follows:

The medium employed for the agar dilution MIC assay was Brucella Agar (Becton Dickinson, Sparks, Md. #211086, Lot #9020009) supplemented with hemin (Sigma #H9039-1G, Lot #039K1121), Vitamin $K_1$ (Sigma, Lot #106K1523), and 5% lysed sheep blood (Cleveland Scientific, Lot 41113-6) (1). This medium is referred to as Supplemented Brucella Agar (SBA).

The media were prepared as follows: Brucella agar was weighed and water was added to the final volume minus the volume of the hemin, vitamin K, and lysed sheep blood. The agar was dissolved by boiling. Hemin (5 µg/ml) and vitamin K (1 µg/ml) were added to the agar and it was autoclaved for 23 minutes at 121° C. The agar was allowed to cool to 50° C. and 18.5 ml was dispensed into sterile glass tubes. Immediately prior to pouring the plates 1 ml of lysed sheep blood and 0.5 ml of the appropriate drug dilution were added to the tube. The contents of the tube were gently mixed by inverting the tube, and the drug-supplemented agar was poured into a petri

TABLE 2

Antibacterial Activity

| Strain | MIC-100 (µg/mL) | | | | |
|---|---|---|---|---|---|
| | Composition A | Composition B | Penicillin G | Clarithromycin | Ciprofloxacin |
| Bacillus subtilis (MB964) | 0.12 | NT | <0.06 | 0.06 | 0.06 |
| Staphylococcus aureus (MB2865) | 2 | NT | <0.06 | 0.12 | 0.12 |
| Staphylococcus aureus (MB5957) | 1 | 16 | NT | NT | 1 |
| Enterococcus faecalis (CL8516) | 2 | NT | 0.5 | 2 | 2 |
| Escherichia coli envA1 tolC (MB5746) | 32 | NT | 8 | 0.12 | <0.015 |
| Streptococcus pneumoniae (CL2883) | 1 | NT | <0.06 | 0.03 | 2 |
| Haemophilus influenzae (MB4572) | 2 | NT | 0.25 | 4 | <0.015 |
| Candida albicans (MY1055) | >64 | NT | >64 | >16 | >16 |

Compositions A and B also demonstrated antibacterial activity against various species that are resistant to many known antibiotics such as methicillin-resistant Staphylococcus aureus (MRSA), vancomycin-resistant Enterococcus sp. (VRE), multidrug-resistant Enterococcus faecium, macrolide-resistant Staphylococcus aureus and Staphylococcus epidermidis, and linezolid-resistant Staphylococcus aureus and Enterococcus faecium.

Example 3

Composition A was tested for antibacterial activity against strains of Clostridium difficile. Drug dilutions and drug-supplemented agar plates were prepared manually.

Media & Media Preparation

The growth and test media were those recommended by the Clinical and Laboratory Standards Institute (CLSI) for growth and susceptibility testing of anaerobes. See Clinical and Laboratory Standards Institute (CLSI). Methods for Antimicrobial Susceptibility Testing of Anaerobic Bacteria; Approved Standard—Seventh Edition. CLSI document M11-A7 [ISBN1-56238-626-3]. Clinical and Laboratory Standards Institute, 940 West Valley Road, Suite 1400, Wayne, Pa. 19087-1898 USA, 2007.

dish. The drug-supplemented plates were allowed to stand on the bench until solid, then transferred into the Bactron II anaerobic chamber (Sheldon Manufacturing Inc., Cornelius, Oreg.; atmosphere of 5% hydrogen, 5% carbon dioxide, 90% nitrogen) and allowed to pre-reduce for 2 hours prior to inoculation.

Selection and Maintenance of Isolates

The strains used are clinical isolates or reference strains acquired from the American Type Culture Collection (ATCC). In particular, the strains were Clostridium difficile 4381 (ATCC 700057) and Clostridium difficile 4822 (ATCC 43596). The culture was maintained frozen at −80° C. in Brucella broth containing 5 µg/ml hemin, 1 µg/ml vitamin K, 5% lysed horse blood, and 20% glycerol.

Inoculum Preparation

The isolates were subcultured on Supplemented Brucella Agar (SBA) plates (Remel, Lenexa, Kans.; Cat. No. R01255) in a Bactron II anaerobic chamber (Sheldon Manufacturing, Cornelius, Oreg.), and incubated 48 h at 35-36° C. in the Bactron II incubator prior to use in the MIC assay.

Plate Filling

Drug Stock Solutions and Dilutions

Test plates were prepared for each strain as follows. To each well of a 96-well plate (with columns 1-12 and rows A-H), 100 µL of appropriate test medium was added using the Thermal-LabSystems MULTIDROP™ dispenser. The Clinical Laboratory Standards Institute (CLSI) (formerly National Committee for Clinical Laboratory Standards (NCCLS)) formula was used to calculate the amount of dilution needed for a standard solution.

Composition Preparation

The test composition was prepared on a weight basis. Composition A was dissolved in DMSO and the stock concentration was 2560 µg/mL was used for testing. Metronidazole and vancomycin (both from Sigma, St. Louis, Mo.), the control compounds, were prepared at a stock concentration of 1280 µg/mL in 100% DMSO.

Plate Inoculation and Activity Determination

The assay was conducted per the reference agar dilution method described by CLSI. See Clinical and Laboratory Standards Institute (CLSI). *Methods for Antimicrobial Susceptibility Testing of Anaerobic Bacteria; Approved Standard—Seventh Edition*. CLSI document M11-A7 [ISBN1-56238-626-3].

Test and reference isolates were sub-cultured on commercially-prepared SBA agar plates (Cat. No. R01255; Remel, Lenexa, Kans.) in the Bactron II anaerobe chamber and incubated for 48 hours at 35° C. (in the Bactron II anaerobe chamber).

The inocula for the MIC assay were prepared inside the Bactron II anaerobe chamber, as follows. Colonies were harvested with a swab and a cell suspension was prepared in pre-reduced *Brucella* Broth to equal the turbidity of a 0.5 McFarland standard. Each cell suspension was loaded into a well of an inoculum replicating device (Melrose Machine Shop, Woodlyn, Pa.) which delivers approximately 1 to 2 µL per spot onto the agar surface for an inoculum of approximately $10^4$ to $10^5$ colony-forming-units per spot. Loading of the inoculum replicating device, and the inoculation of the plates, took place inside the anaerobe chamber. The inoculated agar plates were allowed to stand with the agar facing up until the inocula were absorbed into the agar. The plates were then inverted and incubated at 35° C. for 48 h in the anaerobic environment of the Bactron II (5% hydrogen, 5% carbon dioxide, 90% nitrogen). The MIC was read per CLSI guidelines.

Following inoculation, the drug-supplemented plates were incubated at 35° C. for 48 h in the anaerobic environment (5% hydrogen, 5% carbon dioxide, 90% nitrogen) of the Bactron II. Plates were read to no growth.

The minimum inhibitory concentration (MIC-100) for all compounds was determined to be the lowest concentration of compound at which there was no visible growth as compared to growth control without drug, as determined after an incubation period of 22 to 24 hours. MICs were obtained in accordance to the CLSI guidelines.

MIC Assay Procedure

Composition A demonstrated antibacterial activity against various strains of *Clostridium difficile*. MIC values of 0.12 µg/ml were observed for Composition A as shown in Table 3. For organism-drug combinations where CLSI quality control criteria exist, the MIC values derived were within the published quality control ranges.

TABLE 3

| | Antibacterial Activity | | |
| --- | --- | --- | --- |
| | MIC (µg/mL) | | |
| Strain | Composition A | Vancomycin | Metronidazole |
| *Clostridium difficile* (ATCC 43596) | 0.12 | 1 | 0.25 |
| *Clostridium difficile* (ATCC 700057) | 0.12 | 2 (0.5-4)[1] | 0.25 (0.125-0.5)[1] |

[1] CLSI quality control range

It will be appreciated that various of the above-discussed and other features and functions, or alternatives thereof, may be desirably combined into many other different systems or applications. Also various presently unforeseen or unanticipated alternatives, modifications, variations or improvements on the above-described and herein claimed subject matter may be subsequently made by those skilled in the art and are also intended to be encompassed by the following claims.

What is claimed is:

1. A method of inhibiting growth of bacteria, the method comprising treating *Clostridium difficile* with an effective amour of one or more purified compounds selected from compounds of formula I and formula II:

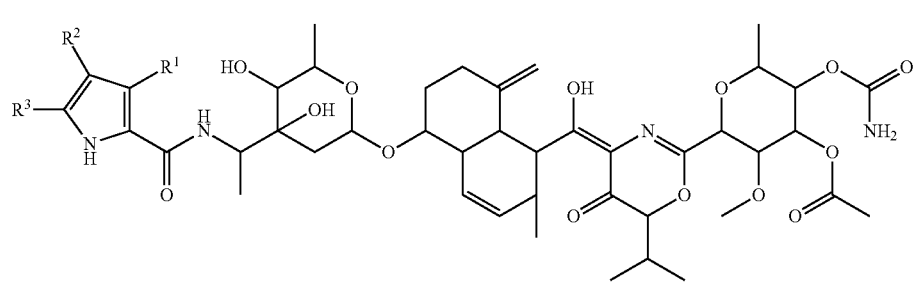

and pharmaceutically acceptable salts thereof,
wherein:
   $R^1$ and $R^2$ are independently selected from the group consisting of hydrogen and halogen; and
   $R^3$ selected from the group consisting of hydrogen and $C_1$-$C_6$ alkyl; and

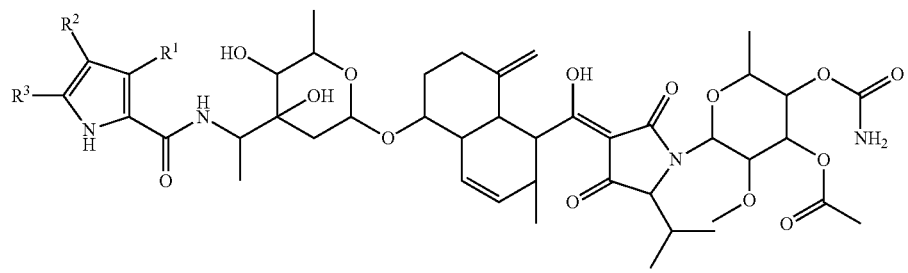

and pharmaceutically acceptable salts thereof, wherein:
$R^1$ and $R^2$ are independently selected from the group consisting of hydrogen and halogen; and
$R^3$ is hydrogen.

2. A method of treating or preventing bacterial infection in a mammalian subject, the method comprising administering to the subject a therapeutically effective amount of one or more purified compounds selected from compounds of formula I and formula II:

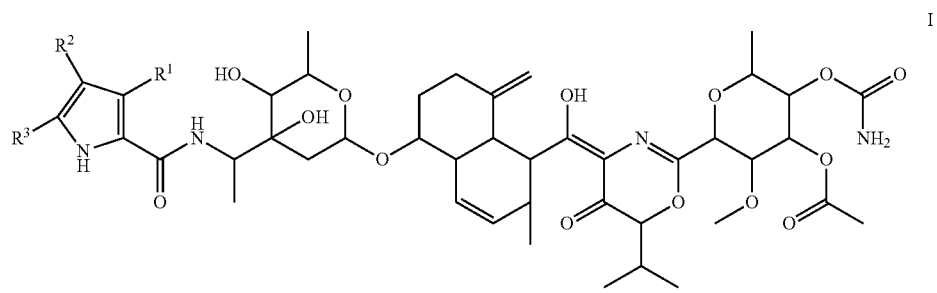

and pharmaceutically acceptable salts thereof,
wherein:
$R^1$ and $R^2$ are independently selected from the group consisting of hydrogen and halogen; and
$R^3$ is selected from the group consisting of hydrogen and $C_1$-$C_6$ alkyl; and

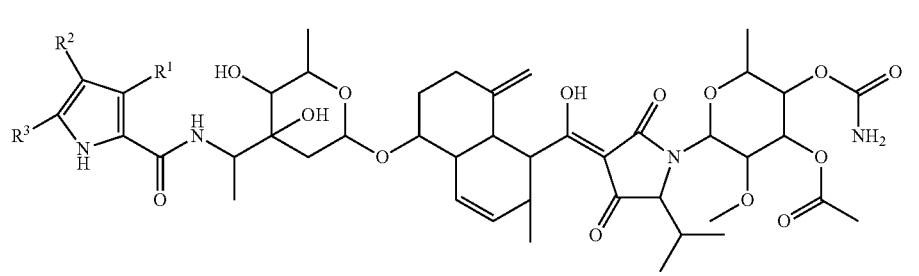

and pharmaceutically acceptable salts thereof, wherein:
$R^1$ and $R^2$ are independently selected from the group consisting of hydrogen and halogen; and
$R^3$ is hydrogen;
wherein said bacterial infection is caused by *Bacillus subtilis, Staphylococcus aureus, Enterococcus faecalis, Escherichia coli, Streptococcus pneumoniae* or *Haemophilus influenzae*.

3. A method of treating or preventing bacterial infection in a mammalian subject, the method comprising administering to the subject a therapeutically effective amount of one or more purified compounds selected from compounds of formula I and formula II:

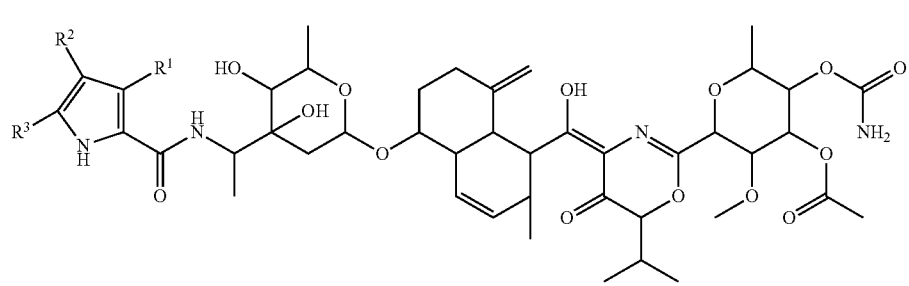

and pharmaceutically acceptable salts thereof,
wherein:
 R$^1$ and R$^2$ are independently selected from the group consisting of hydrogen and halogen; and
 R$^3$ is selected from the group consisting of hydrogen and C$_1$-C$_6$ alkyl; and

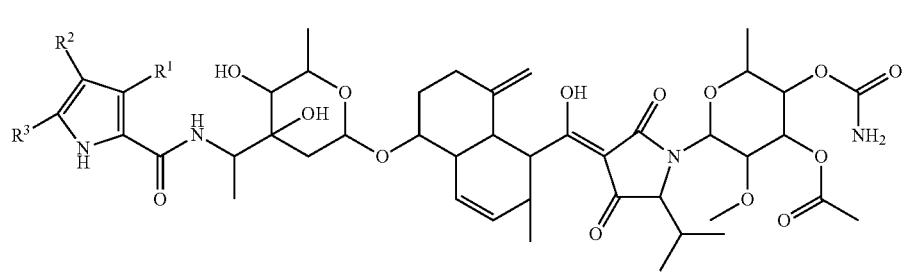

and pharmaceutically acceptable salts thereof, wherein:
 R$^1$ and R$^2$ are independently selected from the group consisting of hydrogen and halogen; and
 R$^3$ is hydrogen
wherein said bacterial infection is caused by *Clostridium difficile*.

4. A method of controlling bacterial infection in a mammalian subject, the method comprising administering to the subject an therapeutically effective amount of one or more purified compounds selected from compounds of formula I and formula II:

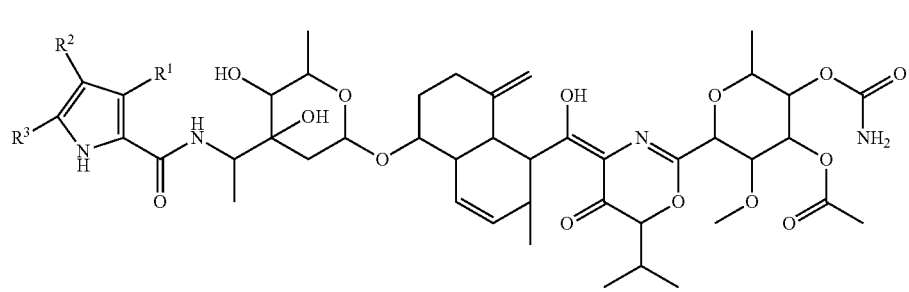

and pharmaceutically acceptable salts thereof,
wherein:
 R$^1$ and R$^2$ are independently selected from the group consisting of hydrogen and halogen; and
 R$^3$ is selected from the group consisting of hydrogen and C$_1$-C$_6$ alkyl; and

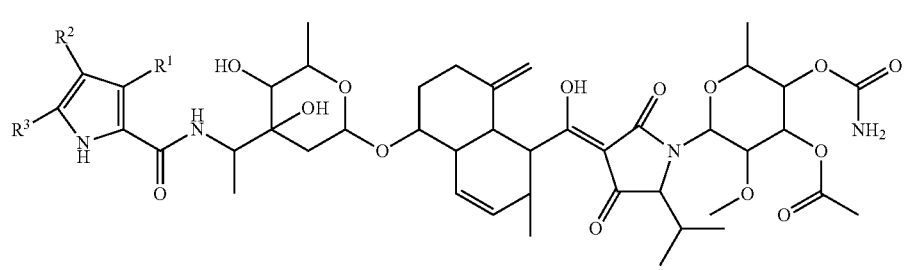

and pharmaceutically acceptable salts thereof, wherein:
$R^1$ and $R^2$ are independently selected from the group consisting of hydrogen and halogen; and
$R^3$ is hydrogen; and
wherein said bacterial infection is caused by *Bacillus subtilis, Staphylococcus aureus, Enterococcus faecalis, Escherichia coli, Streptococcus pneumoniae* or *Haemophilus influenzae.*

5. A method of controlling bacterial infection in a mammalian subject, the method comprising administering to the subject an therapeutically effective amount of one or more purified compounds selected from compounds of formula I and formula II:

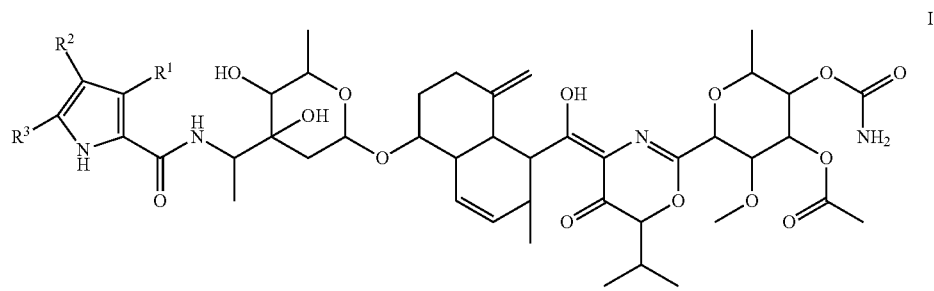

and pharmaceutically acceptable salts thereof,
wherein:
$R^1$ and $R^2$ are independently selected from the group consisting of hydrogen and halogen; and
$R^3$ is selected from the group consisting of hydrogen and $C_1$-$C_6$ alkyl; and

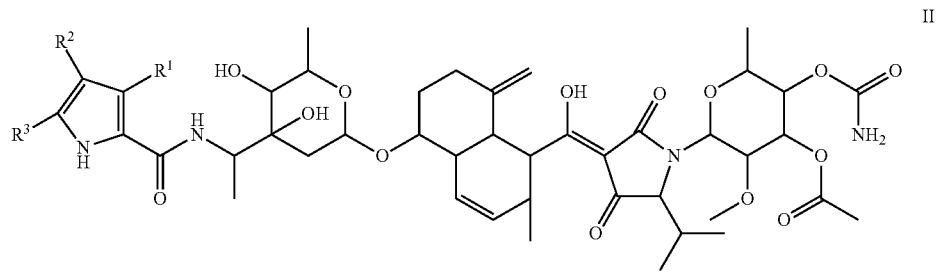

and pharmaceutically acceptable salts thereof, wherein:
$R^1$ and $R^2$ are independently selected from the group consisting of hydrogen and halogen; and
$R^3$ is hydrogen; and
wherein said bacterial infection is caused by *Clostridium difficile.*

* * * * *